(12) United States Patent
Larry

(10) Patent No.: US 11,548,023 B2
(45) Date of Patent: Jan. 10, 2023

(54) HAND SANITIZER DISPENSER FOR VEHICLES

(71) Applicant: Mary Larry, Maywood, IL (US)

(72) Inventor: Mary Larry, Maywood, IL (US)

(*) Notice: Subject to any disclaimer, the term of this patent is extended or adjusted under 35 U.S.C. 154(b) by 0 days.

(21) Appl. No.: 17/680,457

(22) Filed: Feb. 25, 2022

(65) Prior Publication Data

US 2022/0288616 A1 Sep. 15, 2022

Related U.S. Application Data

(60) Provisional application No. 63/155,503, filed on Mar. 2, 2021.

(51) Int. Cl.
  *B05B 11/00* (2006.01)
(52) U.S. Cl.
  CPC ...... *B05B 11/3095* (2013.01); *B05B 11/3073* (2013.01)
(58) Field of Classification Search
  CPC .................. B05B 11/3095; B05B 11/3073
  See application file for complete search history.

(56) References Cited

U.S. PATENT DOCUMENTS

| 4,352,461 A * | 10/1982 | Orta .................. B60R 15/00 428/905 |
| 7,722,431 B2 * | 5/2010 | Sullivan .............. A63H 13/005 40/411 |
| D707,613 S * | 6/2014 | Sanberg .................. D12/220 |
| 2010/0024263 A1 * | 2/2010 | Price .................. A63H 3/50 40/421 |
| 2011/0303695 A1 * | 12/2011 | Fern .................. A61B 90/80 222/52 |
| 2012/0234862 A1 * | 9/2012 | Kharbanda ............. B05B 15/62 222/173 |
| 2016/0221019 A1 * | 8/2016 | Bassett ............... B05B 11/3042 |

* cited by examiner

*Primary Examiner* — Jeremy Carroll
(74) *Attorney, Agent, or Firm* — Brennan, Manna & Diamond, LLC

(57) ABSTRACT

The present invention relates to an ornamental tactile sanitizer dispenser device for vehicles. The dispenser device functions to tactilely dispense sanitizer for a user and as an ornamental prayer device. The device can be mounted to a dashboard of the vehicle such that the sanitizer device remains within an arm's reach of the driver, thereby enabling the driver to tactilely obtain sanitizer using one hand while controlling the vehicle using the other hand. The device in one embodiment has a pair of bobblehead prayer hands and in another embodiment has a pair of thumbs up hand design. The device comes in a first variant where a nozzle is manually depressed to obtain sanitizer, and a second variant that includes a proximity sensor to automatically depress the nozzle to dispense sanitizer upon detecting a human hand under a nozzle.

20 Claims, 5 Drawing Sheets

HAND SANITIZER DISPENSER FOR VEHICLES

CROSS-REFERENCE TO RELATED APPLICATION

The present application claims priority to, and the benefit of, U.S. Provisional Application No. 63/155,503, which was filed on Mar. 2, 2021 and is incorporated herein by reference in its entirety.

FIELD OF THE INVENTION

The present invention relates generally to the field of hand dispenser devices. More specifically, the invention relates to a tactile hand sanitizer dispenser tool for a vehicle that also functions as an ornamental prayer device. The device includes a refillable hand sanitizer storage for dispensing sanitizer upon pressing a nozzle of the tool. The device also has a pair of prayer hands with built-in springs that are configured to move like a bobblehead. The dispenser tool can be mounted to a dashboard of a vehicle such that the dispenser tool remains within an arm's reach of the driver of the vehicle and can be tactilely accessed sans visual contact. Accordingly, the present disclosure makes specific reference thereto. Nonetheless, it is to be appreciated that aspects of the present invention are also equally applicable to other like applications, devices and methods of manufacture.

BACKGROUND

By way of background, use of disinfecting solution and sanitizers have become prevalent especially in the time of pandemics such as Covid-19. Use of a sanitizer becomes more important when a person is away from the home (i.e. traveling in a vehicle to a destination). Individuals generally use sanitizers before eating, after touching a contaminant (or a public) surface, for example. Individuals carry sanitizer containers, bottles, and disposable sachets for use.

Also, it is a common practice for individuals to eat a snack while driving a vehicle. While commuting for long hours, individuals eat snacks at repeated intervals and sanitize their hands before and after having the snacks. As sanitizers conventionally come in bottles, containers, and sachets that require both hands of a user, and visual contact, to access and apply sanitizer on the hands, such sanitizer storage devices are difficult to use in a moving vehicle by a driver. Moreover, typically the user commuting or driving the vehicle needs to search through a glove compartment, purse, backpack, or their pockets to locate hand sanitizer which is time consuming, dangerous, and frustrating. Searching for sanitizer, and then opening the container storing the sanitizer, can be dangerous for the driver which may result in a serious accident. Due to the process of searching for sanitizer, drivers ignore the safety hygiene of applying sanitizer on their hands which can be detrimental to their health. Individuals desire a sanitizer device that does not require them to open a bottle or container while driving a vehicle to access sanitizer for disinfecting their hands.

Sanitizers generally contain more than 70% alcohol in their composition, and therefore, there is a safety hazard storing conventional sanitizer containers in a locked vehicle (especially a car) due to high temperatures developed inside the car because of the greenhouse effects. Sanitizers stored in conventional plastic bottles and containers may reach high temperatures when kept in a locked vehicle and can evaporate rapidly. Alcohol evaporates at a much faster rate compared with water due to its lower boiling temperature. In a given amount of time much more alcohol evaporates than water, Individuals desire a sanitizer storing device that can safely store sanitizer even in locked car at high temperatures.

Individuals love the interiors of their cars and vehicles, and deploy decorative items to enhance the appearance of their vehicles from inside. Therefore, individuals would desire a sanitizer device that not only serves the purpose of easy and safe dispensing and storage of sanitizer but also enhances the interior of the vehicle.

Therefore, there exists a long felt need in the art for a hand sanitizer dispenser for a vehicle that is tactilely accessed, ornamental and which easily dispenses sanitizing solution. There is also a long felt need in the art for a hand sanitizer dispenser that is convenient and easy to use. Additionally, there is a long felt need in the art for a sanitizer dispensing tool for a vehicle that enables a driver to easily release and access sanitizer from the dispenser without using both hands. Moreover, there is a long felt need in the art for hand sanitizer dispensing tool for a vehicle that eliminates searching for a sanitizer container in a glove compartment, purse, backpack, pocket, and other places. Further, there is a long felt need in the art for a tactile hand sanitizer dispensing tool that can be used for releasing sanitizer by a driver without diverting the eyes away from the road. Furthermore, there is a long felt need in the art for a sanitizer dispenser device for a vehicle that stores the sanitizer in a safe manner even in high temperatures in a locked vehicle. Finally, there is a long felt need in the art for a unique and decorative hand sanitizer dispenser for a vehicle that always remains within an arm's reach of the driver to ensure personal hygiene and safety.

The subject matter disclosed and claimed herein, in one embodiment thereof, comprises a hand sanitizer dispenser device tactilely accessed and ornamentally constructed for use with a vehicle. The dispenser device can be combined as a hand sanitizer dispenser and ornamental prayer device for the vehicle and can be installed on a dashboard of the vehicle so that the dispenser device remains within an arm's reach of the driver of the vehicle. The dispenser device has a suction base for mounting the device to the dashboard of the vehicle, a refillable sanitizer storage space within a central shaft of the device for storing hand sanitizer, a nozzle configured to be depressed by a user allowing the device to tactilely dispensing hand sanitizer from a spout of the device, and a pair of curved arms extending in opposite directions of the shaft, wherein each curved arm has a three dimensional hand in an upright position with open fingers and thumb. Each three-dimensional hand is further configured to have a built-in spring enabling the hand to move like a bobblehead when the vehicle is in a moving state or when the nozzle is depressed by the user.

In this manner, the hand sanitizer dispensing tool of the present invention for a vehicle accomplishes all of the forgoing objectives and provides users with a decorative hand sanitizer dispenser installed on a vehicle dashboard. The tool can be refilled with hand sanitizer solution and offers the sanitizing solution to the driver and fellow passenger within an arm's reach. The tool also provides ornamental appeal inside the vehicle and easy tactile access to the sanitizing solution without removing the driver's eyes from the road.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a hand sanitizer dispenser device tactilely accessed and ornamentally constructed for use with a vehicle. The dispenser device can be combined as a hand sanitizer dispenser and ornamental prayer device for the vehicle and can be installed on a dashboard of the vehicle so that the dispenser device remains within an arm's reach of the driver of the vehicle. The dispenser device has a suction base for mounting the device to the dashboard of the vehicle, a refillable sanitizer storage space within a central shaft of the device for storing hand sanitizer, a nozzle configured to be depressed by a user allowing the device to tactilely dispense hand sanitizer from a spout of the device, and a pair of curved arms extending in opposite directions of the shaft wherein each curved arm has a three dimensional hand in an upright position with open fingers and thumb. Each three-dimensional hand is further configured to have a built-in spring enabling the hand to move like a bobblehead when the vehicle is in a moving state or when the nozzle is depressed by the user.

In yet another embodiment, a touchless hand sanitizer ornamental dispenser device for a vehicle is disclosed. The dispenser device includes a central shaft having a refillable storage space for sanitizer solution, a proximity sensor disposed on a spout of the device wherein the device automatically dispenses a desired amount of sanitizer solution when the proximity sensor detects motion/position of hand of a user under the spout. The device for decorative purposes has a pair of 3-D upright hands with built-in springs wherein each 3-D upright hand is attached to a curved arm extending from the central shaft. The 3-D upright hands are configured to have a bobblehead movement using the built-in springs.

In yet another embodiment, the dispenser device has a pair of thumbs up design hands for encouraging the driver of the vehicle.

In yet another embodiment, the pair of prayer hands are available in a pair of ethnicities, nationalities and races.

In yet another embodiment, the decorative hand sanitizer dispenser of the present invention is installed on a vehicle dashboard via a suction cup base.

In yet another embodiment, the dispenser tool is made from an insulated material for prohibiting the stored sanitizer solution from reaching elevated temperatures.

In yet another embodiment, the dispenser tool maintains the temperature of the stored sanitizer in the range between 0 and 30 degrees Celsius.

In yet another embodiment, a one-handed method of dispensing a hand sanitizer solution from a hand sanitizer ornamental dispenser tool is described. The method includes the steps of mounting the dispenser tool on a dashboard of a vehicle such that the tool is within an arm's reach of a driver of the vehicle, tactilely orienting the hand relative to a nozzle, pushing the nozzle by the driver while driving the vehicle, using a thumb while placing the palm below a nozzle spout of the tool to receive the dispensed sanitizer, wherein the tool has a pair of bobblehead 3-D upright hands acting as ornamental prayer hands.

Advantageously, the ornamental hand sanitizer dispenser includes the refillable sanitizer storage that is refillable or rechargeable using a replenishment sanitizer solution or a replacement cartridge. Further, the dispenser requires a user to only use one hand to orient and receive the sanitizer in the hand without diverting eyes away from the road while driving.

Numerous benefits and advantages of this invention will become apparent to those skilled in the art to which it pertains upon reading and understanding of the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
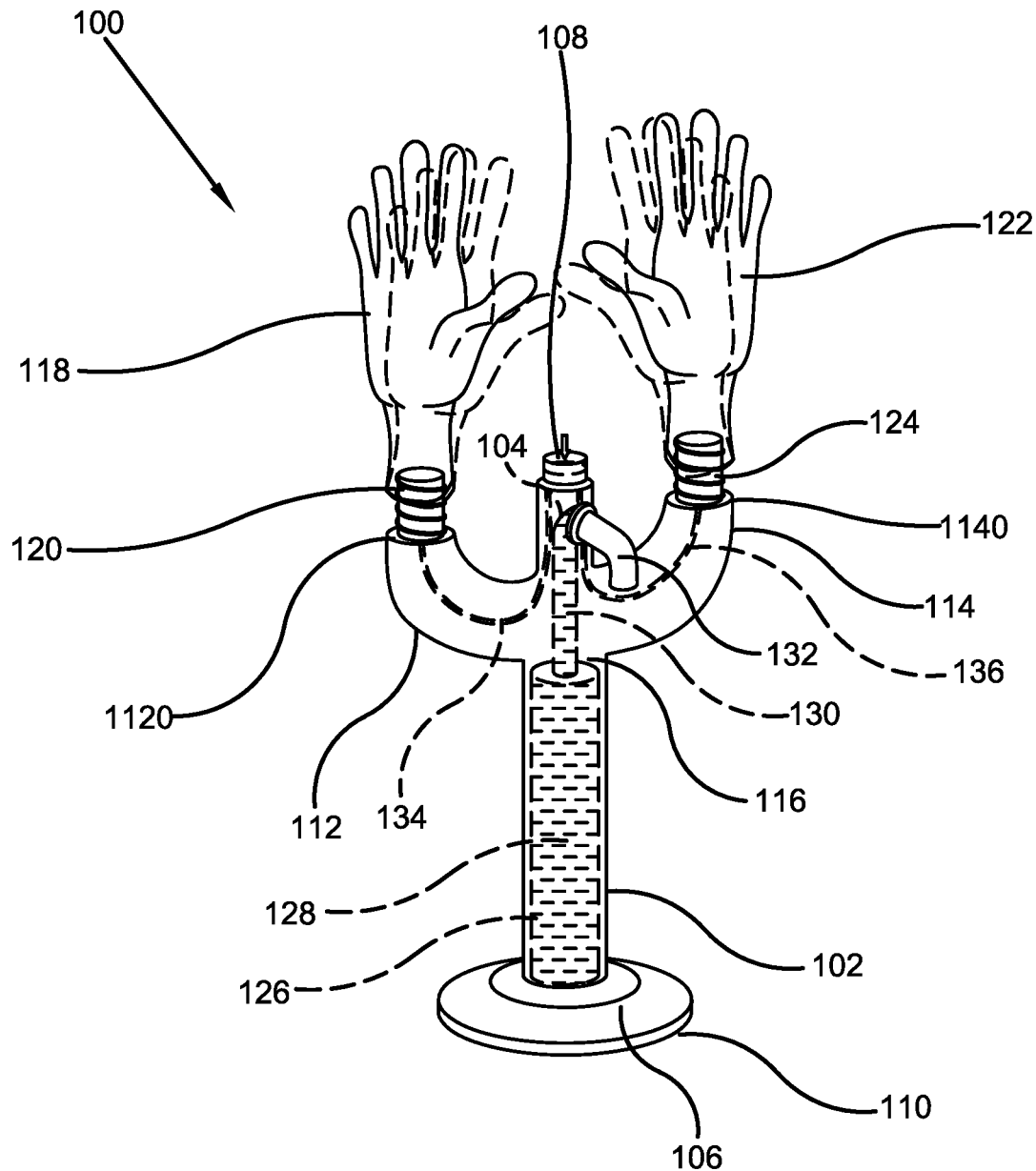
FIG. 1 illustrates a perspective view of one potential embodiment of a hand sanitizer dispensing tool of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long felt need in the art for a hand sanitizer dispenser for a vehicle that is tactilely accessed, ornamental and which easily dispenses sanitizing solution. There is also a long felt need in the art for a hand sanitizer dispenser that is convenient and easy to use. Additionally, there is a long felt need in the art for a sanitizer dispensing tool for a vehicle that enables a driver to easily release and access sanitizer from the dispenser without using both hands. Moreover, there is a long felt need in the art for hand sanitizer dispensing tool for a vehicle that eliminates searching for a sanitizer container in glove compartment, purse, backpack, pockets, and other places. Further, there is a long felt need in the art for a tactile hand sanitizer dispensing tool that can be used for releasing sanitizer by a driver without diverting the eyes away from the road. Furthermore, there is a long felt need in the art for a sanitizer dispenser device for a vehicle that stores the sanitizer in a safe manner even in high temperatures in a locked vehicle. Finally, there is a long felt need in the art for a unique and decorative hand sanitizer dispenser for a vehicle that always remains within an arm's reach of the driver to ensure personal hygiene and safety.

The present invention, in one exemplary embodiment, is a novel touchless hand sanitizer ornamental dispenser device for a vehicle. The dispenser device includes a central shaft having a refillable storage space for sanitizer solution, a proximity sensor disposed on a spout of the device, wherein the device automatically dispenses a desired amount of sanitizer solution when the proximity sensor detects motion of a hand of a user under the spout. The device for decorative purposes has a pair of 3-D upright hands with built-in springs wherein each 3-D upright hand is attached to a curved arm extending from the central shaft. The 3-D upright hands are configured to have a bobblehead movement using the built-in springs.

Figure 3:
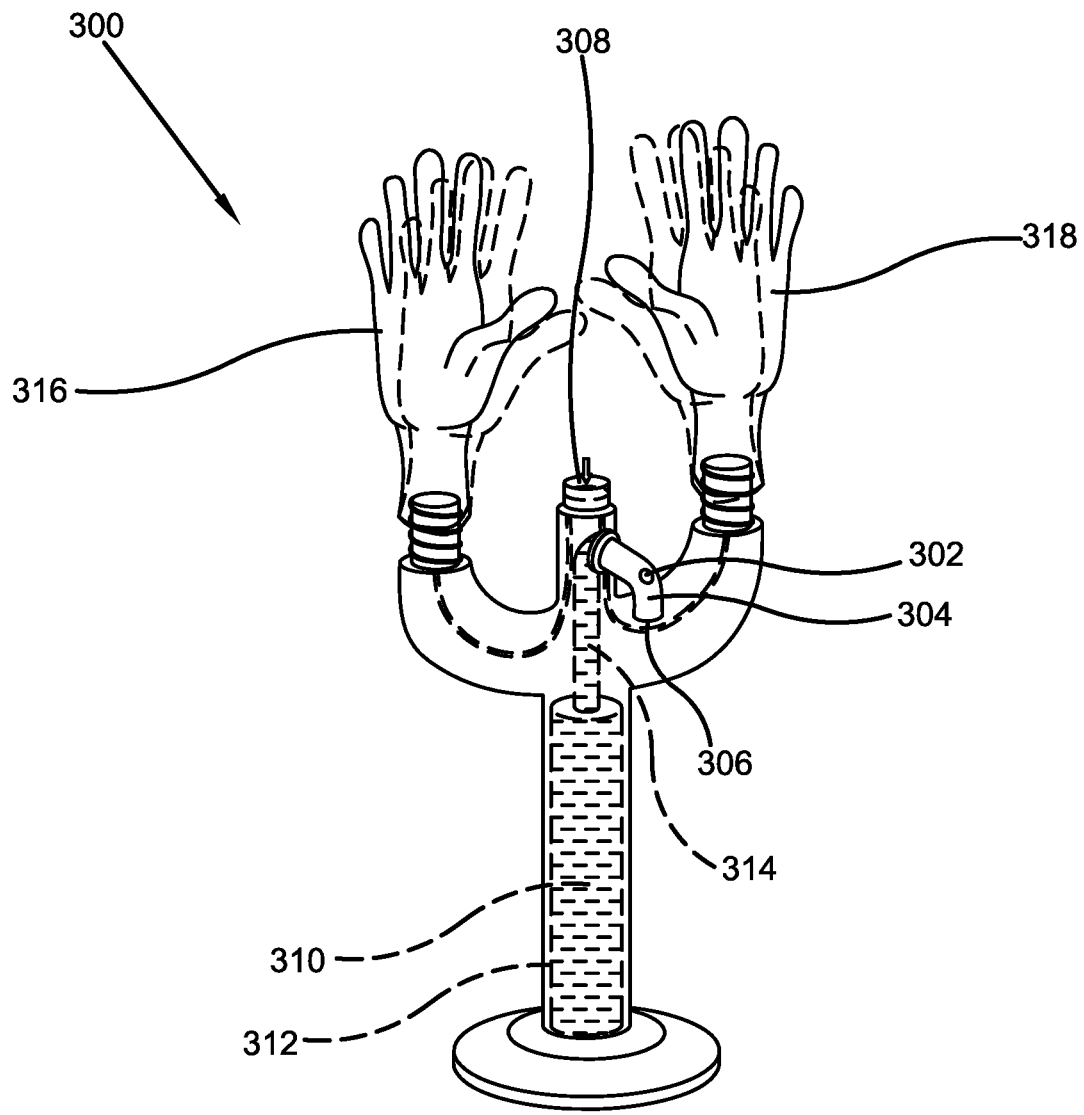
FIG. 3 illustrates a perspective view of a touchless version of the hand sanitizer dispensing tool of FIG. 1 in accordance with the disclosed architecture.

Referring initially to the drawings, FIG. 1 illustrates a perspective view of one potential embodiment of the hand sanitizer dispensing tool of the present invention in accordance with the disclosed architecture. The hand sanitizer dispensing tool 100 is designed as a combination of a tactile hand sanitizer dispenser and ornamental prayer device for vehicles. The tool 100 is ergonomically and tactilely designed in an aesthetic manner to deliver the desired quantity of sanitizer in a consumer's hand without the consumer having to pick up the tool 100. More specifically, the tool 100 includes a central shaft 102 having a top end 104 and a bottom end 106. A dispenser nozzle 108 is disposed proximal to the top end 104 and a suction cup base 110 is disposed proximal to the bottom end 106. The suction cup base 110 is designed to install the tool 100 on a dashboard of a vehicle as best shown in FIG. 3, thereby enabling a driver of the vehicle to access the sanitizer from the tool 100 without diverting the eyes away from the road and without necessitating the use of both hands.

A pair of opposing arms 112,114 extend in opposite directions on either side of the shaft 102 from a common or central point 116 positioned on the shaft 102. A three-dimensional right hand 118 is attached to the free end 1120 of the first arm 112 through a first spring 120. The first spring 120 enables the three-dimensional right hand 118 to move like a bobblehead when the vehicle moves and when the nozzle 108 is depressed by a user. Similarly, a three-dimensional left hand 122 is attached to the free end 1140 of the second arm 114 through a second spring 124. The second spring 124 enables the three-dimensional left hand 122 to move like a bobblehead when the vehicle moves and when the nozzle 108 is depressed by a user.

The shaft 102 has a sanitizer solution refillable container 126 configured to store sanitizer 128. The container 126 is fluidly coupled to the nozzle 108 through a suction pipe 130 that enables the sanitizer 128 to move up from the container 126 towards the nozzle 108 and dispense from the spout 132. The nozzle 108, when depressed by a user, enables the sanitizer 128 to dispense from the spout 132 for use. It should be appreciated that a user can press the nozzle 108 using a single hand to access a desired amount of sanitizer solution and thus eliminates use of both hands to operate the nozzle 108. For refilling or replenishing the sanitizer solution, the container 126 can be replaced or removed from shaft 102 by removing arms 112,114 from the common or central connection point 116.

The three-dimensional right hand 118 and the three-dimensional left hand 122 are configured to move like a bobblehead as a decorative item when the vehicle in which the tool 100 is installed is moving or when the nozzle 108 is depressed by the user. The nozzle 108 is coupled to the first spring 120 via a first metal wire 134 and coupled to the second spring 124 via a second metal wire 136. The metal wires 134,136 allow the nozzle to actuate the springs 120, 124 respectively when the nozzle 108 is depressed even in a stationary vehicle. The hands 118,122 can comprise various ethnicities, nationalities and races to meet requirements of different users.

The tool 100 is made from an insulating and durable material, thereby not allowing the sanitizer to become hot when the vehicle in which the tool 100 is deployed is standing in a locked state in hot weather. The tool 100 can withstand high temperature caused due to greenhouse effect developed in a locked vehicle, thereby protecting the vehicle and user from hazards due to the flammable nature of alcohol constituent of the sanitizer solution. The insulating material also prohibits the sanitizer from freezing in low temperatures.

Figure 2:
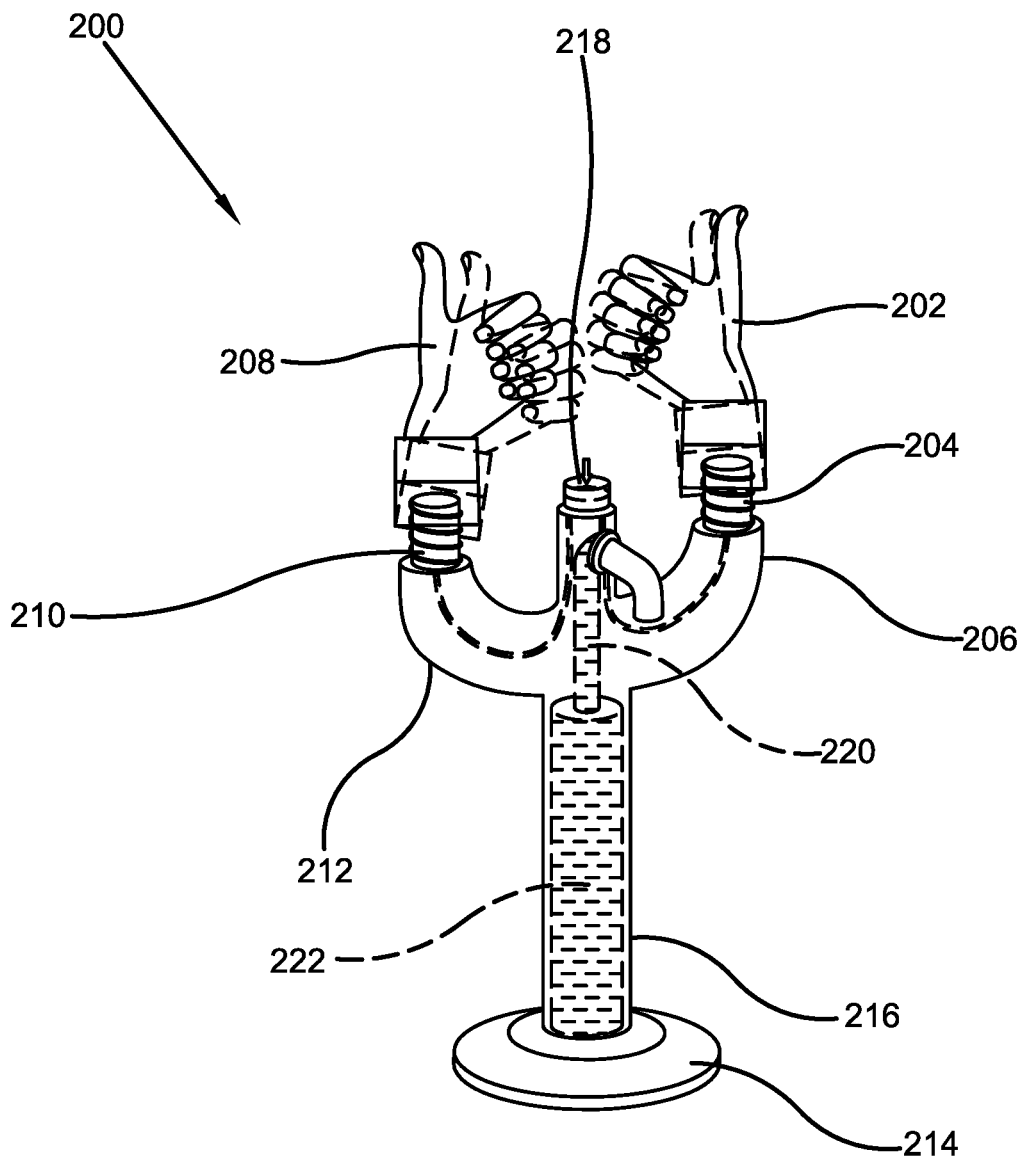
FIG. 2 illustrates a perspective view of another embodiment of the hand sanitizer dispensing tool of the present invention in accordance with the disclosed architecture.

FIG. 2 illustrates a perspective view of another embodiment of the hand sanitizer dispensing tool of the present invention in accordance with the disclosed architecture. In the present embodiment, the sanitizer dispensing ornamental tool 200 has a right thumbs up hand design 202 with built-in first spring 204 attached to the first curved arm 206 and has a left thumbs up hand design 208 with built-in second spring 210 attached to the second curved arm 212. The thumbs up designs 202, 208 are designed to move like bobbleheads when the vehicle in which the tool 200 is deployed is in a moving state. The thumbs up designs 202, 208 are configured to provide encouragement to the driver with their sideways movements. The other functional components such as the suction base 214, shaft 216, nozzle 218, suction pipe 220 and sanitizer storage 222 functions in a similar manner as described in FIG. 1 for carrying sanitizer from the storage 222 to the spout 224 for dispensing upon actuation of the nozzle 218.

FIG. 3 illustrates a perspective view of a touchless version of the hand sanitizer dispensing tool of FIG. 1 in accordance with the disclosed architecture. In the present embodiment, the touchless sanitizer dispensing tool 300 includes a proximity sensor 302 on the spout 304 of the tool 300 for detecting hand motion of a user underneath the opening 306 of the spout 304. Upon detecting a hand, the proximity sensor 302 automatically actuates the nozzle 308 to release the sanitizer gel 310 for use. The sanitizer 310 moves upwards from the storage 312 via the suction pipe 314 towards the spout 304.

The proximity sensor 302, in the present embodiment, detects the infrared energy emitted by the user's hand. When the hand is placed in the proximity of the sensor 302 (underneath the spout opening 306), the infrared energy detected by the sensor 302 quickly fluctuate and the sensor 302 triggers the nozzle 308 to actuate and dispense a designated amount of sanitizer 310 for use.

The three-dimensional right hand 316 and the three-dimensional left hand 318 are configured to move like a bobblehead as an attention 'getter' and decorative item when the vehicle in which the tool 300 is installed is moving or when the nozzle 308 is depressed by the user.

Figure 4:
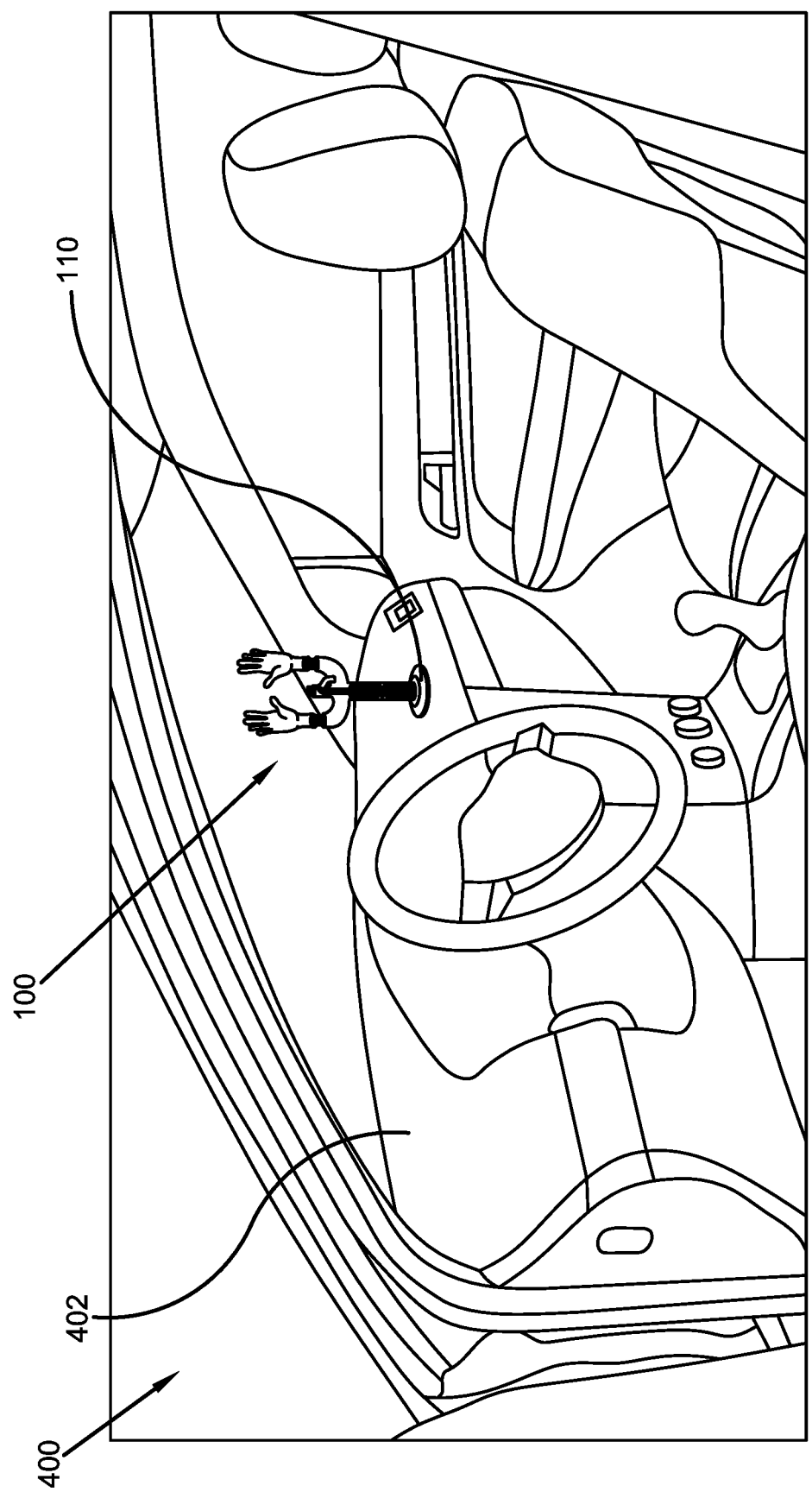
FIG. 4 illustrates a perspective view of the sanitizer dispensing tool of the first embodiment mounted to a dashboard of a car in accordance with the disclosed architecture.

FIG. 4 illustrates a perspective view of the sanitizer dispensing tool 100 of the first embodiment mounted to a dashboard of a car in accordance with the disclosed architecture. As shown, the tool 100 is mounted to the dashboard 402 of the vehicle 400 using the suction cup base 110, thereby safely securing the tool 100 to the dashboard 402. The tool 100 when mounted, is less than one arm distance away from the driver of the vehicle, thereby allowing the driver to use a single hand to take out sanitizer from the device 100 and without diverting eyes from the road while accessing the sanitizer during driving the vehicle.

Figure 5:
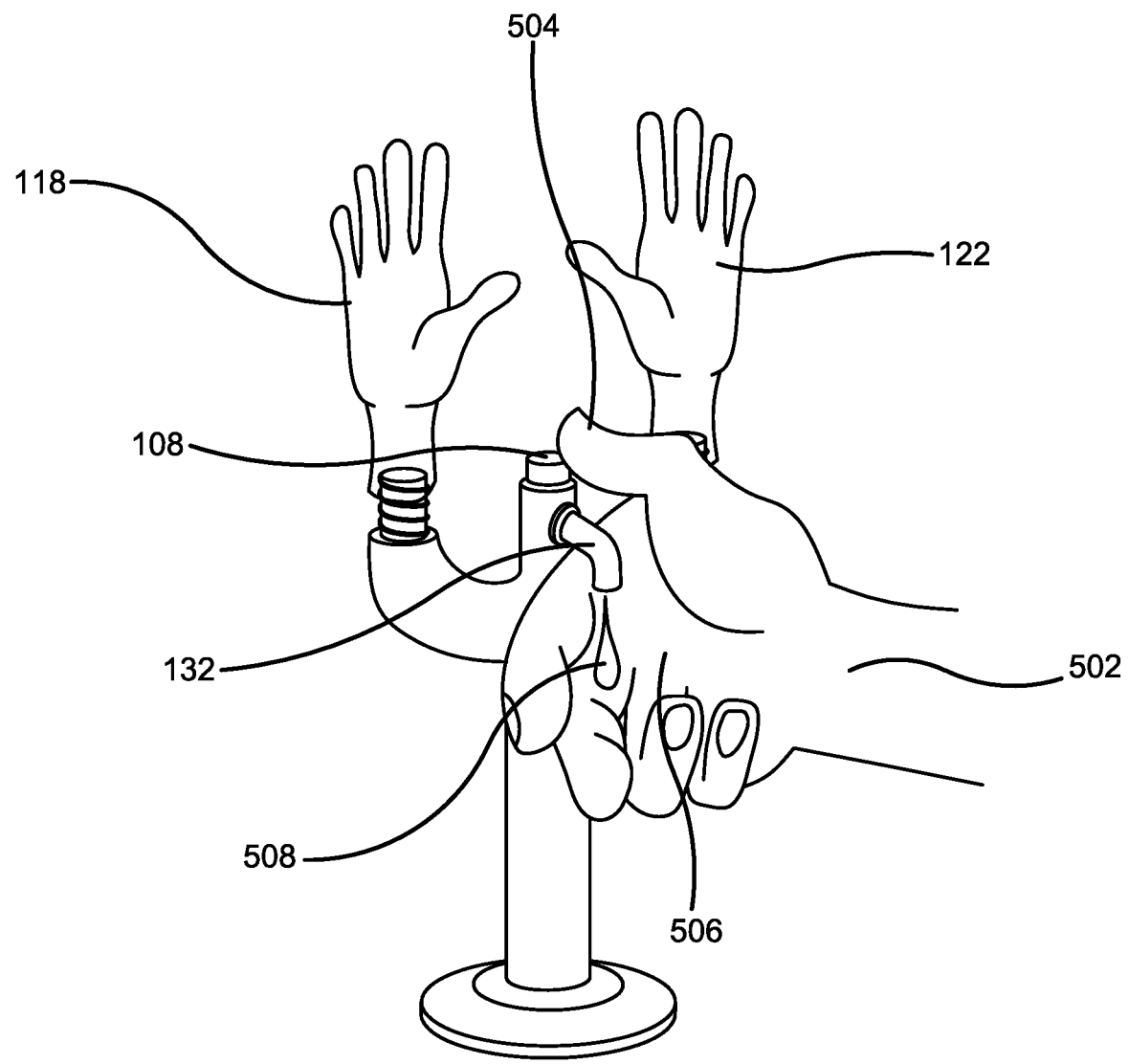
FIG. 5 illustrates a perspective view showing a user obtaining hand sanitizer from the device using one hand in accordance with the disclosed architecture.

FIG. 5 illustrates a perspective view showing a user obtaining hand sanitizer from the device 100 using one hand in accordance with the disclosed architecture. As shown, one hand 502 of a user can be used for obtaining hand sanitizer 510 from the device 100 enabling the user to use the other hand for driving the vehicle, thereby ensuring the safety of the driver. In use, the nozzle 108 is depressed by the thumb 504 while the palm 506 is positioned below the spout 132 to obtain the dispensed sanitizer 508 from the device 100.

When the nozzle 108 is depressed, the 3-D hands 118,122 vibrate sideways to illustrate encouragement and entertainment for the user obtaining the sanitizer from the device 100.

The sanitizer dispensing ornamental tools of various embodiments can vary in shapes, designs, and dimensions. The hands may be designed in various gestures and ethnicities, nationalities and races. The tool of various embodiments does not require clips or any other mechanical fastener to mount to the dashboard of any vehicle. The dispensing tool is lightweight, portable and can be used with gel and liquid-based sanitizer.

Preferably, all the components of the dispenser tool of various embodiments, can be produced as injection-molded parts, also as injection-molded parts consisting of plastic material that can be recycled. For the sanitizer storage, some other material may be chosen as well.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "hand sanitizer dispensing tool", "sanitizer dispensing ornamental tool", "touchless sanitizer dispensing tool", "tool", "device", and "sanitizer dispensing tool" are interchangeable and refer to the sanitizer dispensing ornamental tool 100,200,300 of the present invention.

Notwithstanding the forgoing, the sanitizer dispensing ornamental tool 100,200,300 of the present invention can be of any suitable size and configuration as is known in the art without affecting the overall concept of the invention, provided that it accomplishes the above-stated objectives. One of ordinary skill in the art will appreciate that the sanitizer dispensing ornamental tool 100, 200, 300 as shown in the FIGS. are for illustrative purposes only, and that many other sizes and shapes of the sanitizer dispensing ornamental tool 100, 200, 300 are well within the scope of the present disclosure. Although the dimensions of the sanitizer dispensing ornamental tool 100, 200, 300 are important design parameters for user convenience, the sanitizer dispensing ornamental tool 100, 200, 300 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An dispenser device for dispensing a sanitizer, the dispenser device comprising:
    a central shaft including a top end and a bottom end;
    a dispenser nozzle proximal to said top end;
    a suction cup base proximal to said bottom end for mounting to a vehicle surface near a driver;
    a pair of opposing arms extending in opposite directions on either side of said central shaft from a central position on said central shaft;
    a three-dimensional (3D) first object attached to a free end of a first arm with a first spring;
    a three-dimensional (3D) second object attached to a free end of a second arm with a second spring;
    said central shaft includes a sanitizer solution container for storing the sanitizer;
    said container fluidly coupled to said nozzle through a suction pipe for enabling said sanitizer to move up from said container towards said nozzle and dispense from a spout; and
    further wherein said 3D first object and said 3D second object tactilely orient a driver's thumb to said nozzle and a driver's hand to under said spout for dispensing said sanitizer without visual contact with said dispenser device.

2. The dispenser device of claim 1, wherein said 3D first object is in the shape of a right hand.

3. The dispenser device of claim 2, wherein said 3D second object is in the shape of a left hand.

4. The dispenser device of claim 3, wherein said second spring enables said 3D second object to move when the vehicle moves and when said nozzle is depressed by the driver.

5. The dispenser device of claim 4, wherein said nozzle connected to said first spring with a first metal wire and connected to said second spring with a second metal wire, further wherein said first metal wire and said second metal wire actuate said first spring and said second spring when said nozzle is depressed.

6. The dispenser device of claim 2, wherein said first spring enables said 3D first object to move when the vehicle moves and when said nozzle is depressed by the driver.

7. The dispenser device of claim 1, wherein depressing said nozzle dispenses said sanitizer from said spout.

8. The dispenser device of claim 7, wherein said depressing said nozzle is with a single driver's hand.

9. The dispenser device of claim 8, wherein said container is removable from said central shaft for replenishing said sanitizer.

10. The dispenser device of claim 9, wherein said container is insulated for insulating said sanitizer from extreme heat and extreme cold.

11. A dispenser device for dispensing a sanitizer, the dispenser device comprising:
    a central shaft including a top end and a bottom end;
    a dispenser nozzle proximal to said top end;
    a suction cup base proximal to said bottom end for mounting to a vehicle surface near a driver;
    a pair of opposing arms extending in opposite directions on either side of said central shaft from a central position on said central shaft;
    a three-dimensional (3D) first object attached to a free end of a first arm with a first spring;
    a three-dimensional (3D) second object attached to a free end of a second arm with a second spring;
    said central shaft includes a sanitizer solution container for storing the sanitizer;
    said container fluidly coupled to said nozzle through a suction pipe for enabling said sanitizer to move up from said container towards said nozzle and dispense from a spout;
    wherein said 3D first object and said 3D second object tactilely orient a driver's hand to under said spout without visual contact with said dispenser device.

12. The dispenser device of claim 11, wherein said 3D first object is in the shape of a right hand.

13. The dispenser device of claim 12, wherein said 3D second object is in the shape of a left hand.

14. The dispenser device of claim 13, wherein said second spring enables said 3D second object to move when the vehicle moves and when said nozzle is depressed by the driver.

15. The dispenser device of claim 12, wherein said first spring enables said 3D first object to move when the vehicle moves and when said nozzle is depressed by the driver.

16. The dispenser device of claim 11, wherein said depressing said nozzle dispenses a designated amount of said sanitizer from said spout.

17. The dispenser device of claim 16, wherein said container is removable from said central shaft for replenishing said sanitizer.

18. The dispenser device of claim 17, wherein said container is insulated for insulating said sanitizer from heat and cold.

19. A dispenser device for dispensing a sanitizer, the dispenser device comprising:
    a central shaft including a top end and a bottom end;
    a dispenser nozzle proximal to said top end;
    a suction cup base proximal to said bottom end for mounting to a vehicle surface near a driver;
    a pair of opposing arms extending in opposite directions on either side of said central shaft from a central position on said central shaft;
    a three-dimensional (3D) first object attached to a free end of a first arm with a first spring;
    a three-dimensional (3D) second object attached to a free end of a second arm with a second spring;
    wherein said 3D first object is in the shape of a right hand and wherein said 3D second object is in the shape of a left hand;
    wherein said first spring enables said 3D first object to move like a bobblehead when the vehicle moves and when said nozzle is depressed by the driver;
    wherein said second spring enables said 3D second object to move like a bobblehead when the vehicle moves and when said nozzle is depressed by the driver;
    wherein said central shaft includes an insulated sanitizer solution container for storing the sanitizer and for insulating said sanitizer from heat and cold;
    wherein said container fluidly coupled to said nozzle through a suction pipe for enabling said sanitizer to move up from said container towards said nozzle and dispense from a spout; and
    further wherein said 3D first object and said 3D second object tactilely orient a driver's hand to under said spout without visual contact with said dispenser device.

20. The dispensing device of claim 19 further comprising a proximity sensor for detecting the driver's hand under said spout and for automatically depressing said nozzle to dispense said sanitizer into the driver's hand.

* * * * *